United States Patent
Kim et al.

(10) Patent No.: US 11,723,931 B2
(45) Date of Patent: Aug. 15, 2023

(54) COMPOSITION FOR IMPROVING, PREVENTING OR TREATING SKIN DISEASES COMPRISING INDUCED PLURIPOTENT STEM CELL-DERIVED MESENCHYMAL STEM CELL AND EXOSOME DERIVED THEREFROM

(71) Applicants: THE ASAN FOUNDATION, Seoul (KR); UNIVERSITY OF ULSAN FOUNDATION FOR INDUSTRY COOPERATION, Ulsan (KR)

(72) Inventors: Sue Kim, Seoul (KR); Jin Ho Yu, Seoul (KR); Yeon Mok Oh, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 351 days.

(21) Appl. No.: 16/959,175

(22) PCT Filed: Jan. 7, 2019

(86) PCT No.: PCT/KR2019/000180
§ 371 (c)(1),
(2) Date: Jun. 30, 2020

(87) PCT Pub. No.: WO2019/135644
PCT Pub. Date: Jul. 11, 2019

(65) Prior Publication Data
US 2020/0338136 A1    Oct. 29, 2020

(30) Foreign Application Priority Data
Jan. 5, 2018  (KR) .................. 10-2018-0001978

(51) Int. Cl.
*A61K 35/545* (2015.01)
*A61P 17/10* (2006.01)
*A61K 8/98* (2006.01)
*A61K 35/28* (2015.01)
*A61Q 19/00* (2006.01)

(52) U.S. Cl.
CPC ............ *A61K 35/545* (2013.01); *A61K 8/982* (2013.01); *A61K 8/983* (2013.01); *A61K 35/28* (2013.01); *A61P 17/10* (2018.01); *A61Q 19/00* (2013.01)

(58) Field of Classification Search
None
See application file for complete search history.

(56) References Cited

U.S. PATENT DOCUMENTS

2009/0246181 A1    10/2009  Kuroda et al.
2015/0125950 A1*    5/2015  Lim ................... C12N 5/0668
                                                                    435/325

FOREIGN PATENT DOCUMENTS

| KR | 10-2010-0104385 A | 9/2010 |
| KR | 10-2010-0122087 A | 11/2010 |
| KR | 10-2014-0127209 A | 11/2014 |
| KR | 10-2017-0044999 A | 4/2017 |
| WO | WO-2017/165235 A1 | 9/2017 |

OTHER PUBLICATIONS

Sabapathy, V., et al.; "hiPSC-derived iMSCs: NextGen MSCs as an advanced therapeutically active cell resource for regenerative medicine", Journal of cellular and molecular medicine, 2016, 20(8), pp. 1571-1588.

Zhang, Z., et al.; "EGFR Signaling Blunts Allergen-Induced IL-6 Production and Th17 Responses in the Skin and Attenuates Development and Relapse of Atopic Dermatitis", The Journal of Immunology, 2013, 192(3), 859-866.

Ma, X., et al.; "Hypoxia-induced overexpression of stanniocalcin-1 is associated with the metastasis of early stage clear cell renal cell carcinoma", Journal of translational medicine, 2015, 13(1), 49, pp. 1-14.

Hu, G., et al.; "Exosomes secreted by human-induced pluripotent stem cell-derived mesenchymal stem cells attenuate limb ischemia by promoting angiogenesis in mice", Stem Cell Research & Therapy 2015, 6:10.

International Search Report from corresponding PCT Application No. PCT/KR2019/000180, dated May 27, 2019.

EESR of EP Patent Application No. 19735716.3 issued on Feb. 26, 2021.

Boháč, M., et al.; "Stem cell regenerative potential for plastic and reconstructive surgery", Cell Tissue Bank, Sep. 7, 2016, pp. 1-10.

Zhang, J., et al.; "Exosomes released from human induced pluripotent stem cells-derived MSCs facilitate cutaneous wound healing by promoting collagen synthesis and angiogenesis", Journal of Translational Medicine (2015) 13:49.

\* cited by examiner

*Primary Examiner* — Russell G Fiebig
(74) *Attorney, Agent, or Firm* — Harness, Dickey & Pierce, P.L.C.

(57) ABSTRACT

The present invention may provide a pharmaceutical composition for preventing or treating skin diseases, a cosmetic composition for preventing or improving skin diseases, and a stem cell therapeutic agent, which comprise an induced pluripotent stem cell-derived mesenchymal stem cell (iMSC), a culture thereof, or an exosome isolated from an iMSC or iMSC culture as active ingredients. When the composition of the present invention, etc. is used, it is possible to provide a composition for improving, preventing or treating skin diseases and a stem cell therapeutic agent which have an improved immunomodulating function over conventional mesenchymal stem cells.

2 Claims, 14 Drawing Sheets

Specification includes a Sequence Listing.

COMPOSITION FOR IMPROVING, PREVENTING OR TREATING SKIN DISEASES COMPRISING INDUCED PLURIPOTENT STEM CELL-DERIVED MESENCHYMAL STEM CELL AND EXOSOME DERIVED THEREFROM

CROSS-REFERENCE TO RELATED APPLICATIONS

This application is a national phase application of PCT Application No. PCT/KR2019/000180, filed Jan. 7, 2019, which claims benefit of Korean Patent Application No. 10-2018-0001978, filed on Jan. 5, 2018. The entire disclosures of the applications identified in this paragraph are incorporated herein by references.

FIELD

The present invention was made with the support of the Ministry of Science, ICT, and Future Planning of the Republic of Korea, under Project No. NRF-2015K1A4A3046807, which was conducted under the research subject named "Asan-Minnesota Institute for Innovating Transplantation" within the program titled "Leading Foreign Research Institute Recruitment Program" by "Asan Medical Center" under management of the National Research Foundation of Korea, from 1 Sep. 2015 to 31 Aug. 2021.

The present invention relates to a composition comprising induced pluripotency stem cell-derived mesenchymal stem cells (iMSC), a culture thereof, and/or exosomes (iMSC-exo) derived from iMSC or a culture of iMSC as an active ingredient for alleviation, prevention, or treatment of a skin disease.

BACKGROUND

Atopic dermatitis (AD), also known as atopic eczema, is a type of inflammation on the skin, which has become common, affecting 5-20% of children worldwide. It is reported that the pathogenesis of acute AD is associated with Th2 inflammatory responses mediated by the dermal infiltration of CD4+ T cells and eosinophils and the increased release of immunoglobulin E (IgE) and Th2 cytokine. Thus far, a direct specific therapy for AD is still unknown. Thus, there is an urgent need for developing a novel therapeutic method for AD.

Mesenchymal stem cells, which are highly proliferative adherent cells having multipotency to differentiate into bone, cartilage, fat, and the like, are known to have anti-inflammatory and immunomodulatory abilities. Mesenchymal stem cells exhibit immunosuppressive effects by, for example, restraining proliferation and differentiation of T cells and B cells and functionally inhibiting immune cells, such as dendritic cells, natural killer (NK) cells, and macrophages. According to a recent report, mesenchymal stem cells were successfully transplanted together with hematopoietic stem cells to increase engraftment of the hematopoietic stem cells. When used in diseases such as graft-versus-host disease (GVHD), collagen-induced arthritis (CIA), experimental autoimmune encephalomyelitis (EAE), systemic lupus erythematosus, SLE), sepsis, acute pancreatitis (AP), colitis, multiple sclerosis (MS), and rheumatoid arthritis, mesenchymal stem cells were also reported to reduce inflammation and inhibit autoimmune hyperreactivity.

Exosomes, which are lipid-bilayer vesicles, contain matter that cells extracellularly secrete. Exosomes carry (transport) intracellular biomolecules including proteins, bioactive lipids, and RNA (miRNA), thus playing a functional role in mediating cell-to-cell communication and cellular immunity. There is a growing interest in applications of exosomes as a biomarker for a neurological disease, such as Alzheimer's disease and the like. Thanks to their highly selective penetration ability to cross the blood-brain barrier (BBB) that separates cerebrospinal fluid and blood, exosomes are also utilized for developing drug delivery systems, such as nanocarriers of specific drugs.

Exosomes secreted from mesenchymal stem cells are involved in cell-to-cell communication and show therapeutic efficacy of stem cells in regenerative medicine. In recent years, active studies have been conducted about therapeutic effects of exosomes secreted from mesenchymal stem cells, but not mesenchymal stem cells themselves, on various diseases.

Intensive and thorough research, conducted by the present inventors, into the development of mesenchymal stem cells and exosomes thereof into a therapeutic agent for atopic dermatitis resulted in the finding that mesenchymal stem cells (MSC) differentiated from induced pluripotent stem cells (iPSC) [iMSC] exhibit improved anti-inflammatory activity and alleviative effects on skin disease, compared to conventional mesenchymal stem cells and that exosomes derived therefrom (iMSC-Exo) have an alleviative effect on skin disease including atopic dermatitis, leading to the present invention.

SUMMARY

Technical Problem

A purpose of the present invention is to provide a pharmaceutical composition for prevention or treatment of a skin disease, the composition comprising induced pluripotent stem cell (iPSC)-derived mesenchymal stem cells (iPSC-MSC, iMSC); a culture thereof; and/or iPSC-derived mesenchymal stem cell-derived exosomes (iMSC-Exo).

Another purpose of the present invention is to provide a cosmetic composition for prevention or alleviation of a skin disease, the composition comprising iMSC and/or iMSC-Exo.

A further purpose of the present invention is to provide exosomes (iMSC-Exo) isolated from induced pluripotent stem cell-derived mesenchymal stem cells (iMSC) or a culture thereof.

A still further purpose of the present invention is to provide a method for producing exosomes (iMSC-Exo) isolated from induced pluripotent stem cell-derived mesenchymal stem cells.

Still another purpose of the present invention is to provide a stem cell therapy product comprising iMSC and/or iMSC-Exo.

Technical Solution

According to an aspect thereof, the present invention provides a pharmaceutical composition for prevention or treatment of a skin disease, the composition comprising induced pluripotent stem cell (iPSC)-derived mesenchymal stem cells (iMSC); a culture thereof; or exosomes separated from iMSC or a culture of iMSC (iMSC-derived exosome, iMSC-Exo) as an active ingredient.

Intensive and thorough research, conducted by the present inventors, into the development of mesenchymal stem cells having enhanced anti-inflammatory activity resulted in the finding that mesenchymal stem cells differentiated from induced pluripotent stem cells (iPSC) exhibit improved anti-inflammatory activity and alleviative effects on skin disease, compared to conventional mesenchymal stem cells and that the induced pluripotent stem cell-derived mesenchymal stem cells and exosomes derived therefrom (iMSC-Exo) have an alleviative effect on skin disease including atopic dermatitis.

As used herein, the term "induced pluripotent stem cell (iPSC)" refers to a pluripotent cell generated from a differentiated cell, such as a somatic cell, by inducing dedifferentiation to return back to an initial undifferentiated state. The dedifferentiation can be induced by introducing and expressing particular genes (e.g., Sox2, c-Myc, Klf4, Oct-4, or the like) or by injecting a dedifferentiation-inducing protein produced from cells having the particular genes introduced thereinto. The pluripotency describes the ability to differentiate into tissues or organs of the living body to which the three germ layers endoderm, mesoderm, and ectoderm eventually give rise.

The induced pluripotent stem cells of the present invention are intended to encompass induced pluripotent stem cells derived from all mammals, such as humans, monkeys, pigs, horses, cows, sheep, dogs, cats, rats, rabbits, and so on, but with preference to induced pluripotent stem cells derived from humans. As used herein, the term "mesenchymal stem cell" refers to a multipotent stem cell able to differentiate into cells of fat, cartilage, bone, muscle, skin, nerve, and the like. The mesenchymal stem cells may be differentiated from induced pluripotent stem cells or may be isolated from bone marrow, adipose tissue, umbilical cord tissue, umbilical cord blood, skeletal muscle, peripheral blood, synovial, amniotic fluid, or the like.

As used herein, the term "induced pluripotent stem cell-derived mesenchymal stem cell" refers to a mesenchymal stem cell differentiated from an induced pluripotent stem cell (iMSC).

In an embodiment of the present invention, the induced pluripotent stem cell-derived mesenchymal stem cells are characterized by (i) an increased expression level of indoleamine 2,3-dioxygenase and (ii) reduced secretion of an inflammatory cytokines, compared with mesenchymal stem cells isolated from the internal tissues or organs of the body (e.g., bone marrow, adipose tissue, umbilical cord tissue, umbilical cord blood, skeletal muscle, peripheral blood, synovial, amniotic fluid, or the like).

The inflammatory cytokine is at least one inflammatory cytokine selected from the group consisting of IFN-γ, TNF-α, IL-1β, IL-6, and IL-6Rα.

The term "culture", as used herein, is intended to encompass a culture solution obtained by culturing induced pluripotent stem cell-derived mesenchymal stem cells in a broth medium, and a substance obtained by drying, filtering, and/or concentrating the culture solution. The culture may or may not contain the induced pluripotent stem cell-derived mesenchymal stem cells.

As used herein, the term "exosome" refers to a membrane vesicle that is extracellularly secreted from a cell or has a membrane structure composed of a lipid-bilayer present in the cell, and exosomes are found in the body fluid of almost all eukaryotes. Exosomes are about 30 to 1000 nm in diameter. Cells release exosomes directly from cell membranes or when multivesicular bodies are fused to cell membranes. It is well known that exosomes play a functional role in mediating coagulation, cell-cell communication, and cellular immunity by transporting intracellular biomolecules, such as proteins, bioactive lipids, and RNA (miRNA). In the present invention, the exosomes are intended to encompass microvesicles. CD63 and CD81 are known as marker proteins of exosomes. In addition, various proteins including, for example, cell surface receptors such as EGFR, signaling-related molecules, cell adhesion-related proteins, MSC-associated antigens, heat shock proteins, and vesiculation-related Alix are found in exosomes.

In the present invention, exosomes isolated from induced pluripotent stem cell-derived mesenchymal stem cells (iMSC) or a culture thereof refer to exosomes found within the induced pluripotent stem cell-derived mesenchymal stem cells (iMSC) or released from iMSC into the culture (or culture solution).

As used herein, the term "comprising as active ingredient" refers to comprising the induced pluripotent stem cell-derived mesenchymal stem cells, the culture thereof, or the exosomes isolated therefrom in an amount sufficient to attain activity to alleviate, prevent, or treat a skin disease.

As used herein, the term "skin disease" refers to an abnormal condition or symptom occurring in the skin.

In an embodiment of the present invention, the skin disease is an inflammatory skin disease. The inflammatory skin disease means a skin disease that causes symptoms, such as itching and erythema, due to immune cell-mediated inflammatory responses.

In another embodiment of the present invention, the inflammatory skin disease is a skin disease selected from the group consisting of atopic dermatitis, contact dermatitis, and psoriasis.

As used herein, the term "atopic dermatitis" refers to a skin eczema disease, which is a kind of dermatitis characterized by a chronic relapse of severe itching.

As used herein, the term "prevention" refers to all acts of suppressing a skin disease or disorder or delaying the progress of a skin disease or disorder by administering the composition of the present invention.

As used herein, the term "treatment" refers to (a) suppressing the development of a skin disease or disorder; (b) alleviating a skin disease or disorder; and (c) removing a skin disease or disorder.

The composition of the present invention may be prepared into a pharmaceutical composition.

According to a particular embodiment of the present invention, the composition of the present invention is a pharmaceutical composition comprising: (a) a pharmaceutically effective amount of the induced pluripotent stem cell-derived mesenchymal stem cells of the present invention, the culture thereof, or the exosomes isolated therefrom; and (b) a pharmaceutically acceptable carrier. As used herein, the term "pharmaceutically effective amount" refers to an amount sufficient to attain the above-described efficacy or activity of the induced pluripotent stem cell-derived mesenchymal stem cells (iMSC), the culture thereof, or the exosomes isolated from iMSC or iMSC culture.

For preparation into a pharmaceutical composition, the pharmaceutical composition of the present invention comprises a pharmaceutically acceptable carrier. So long as it is typically used for preparing a pharmaceutical composition, any pharmaceutically acceptable carrier may be contained in the pharmaceutical composition of the present invention. Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto. In addition to the above ingredients, the pharmaceutical composition of the present invention may further comprise a lubricant, a humectant, a sweetener, a flavoring agent, an emulsifier, a suspending agent, a preservative, and the like. With regard to proper pharmaceutically acceptable carriers and preparations, reference may be made to *Remington's Pharmaceutical Sciences* (19th ed., 1995).

The pharmaceutical composition of the present invention may be administered orally or parenterally, for example, intravenously, subcutaneously, intramuscularly, intraperitoneally, topically, intranasally, intrapulmonary, rectally, intrathecally, intraocularly, percutaneously, and transdermally.

A suitable dose of the pharmaceutical composition of the present invention may vary depending on various factors including formulation methods, administration methods, the patient's age, body weight, sex, severity of diseases, diet, administration time, administration route, an excretion rate, and sensitivity. The pharmaceutical composition of the present invention is generally administered at a daily dose of 0.0001-1000 mg/kg for an adult, but without limitations thereto.

In an embodiment of the present invention, the dose of the pharmaceutical composition of the present invention may be 0.001-1000 mg/kg, 0.01-1000 mg/kg, 0.1-1000 mg/kg, 1-1000 mg/kg, 5-1000 mg/kg, 10-1000 mg/kg, 20-1000 mg/kg, 30-1000 mg/kg, 50-1000 mg/kg, 100-1000 mg/kg, 0.0001-100 mg/kg, 0.001-100 mg/kg, 0.01-100 mg/kg, 0.1-100 mg/kg, 1-100 mg/kg, 5-100 mg/kg, 10-100 mg/kg, 20-100 mg/kg, 30-100 mg/kg, or 50-100 mg/kg, and more specifically, 1, 5, 10, 15, 20, 25, 30, 35, 40, 45, 50, 55, 60, 65, 70, 75, 80, 85, 90, 95, 100, 150, 200, 250, 300, 350, 400, 450, 500, 750, or 1000 mg/kg.

The pharmaceutical composition of the present invention may be formulated, together with a pharmaceutically acceptable carrier and/or excipient, according to a method that could be easily practiced by a person skilled in the art to which the present invention pertains, and the composition of the present invention may be prepared into a unit dosage form or may be contained in a multi-dose container. In this regard, the formulation may take the form of a solution in an oily or aqueous medium, a suspension, a syrup, an emulsion, an extract, a pulvis, a powder, granules, a tablet, or a capsule and may further comprise a dispersant or a stabilizer.

Another aspect of the present invention provides a cosmetic composition comprising induced pluripotent stem cell (iPSC)-derived mesenchymal stem cells (MSC) [iMSC]; a culture thereof; or exosomes derived from iMSC or a culture of iMSC (iMSC-derived exosome, iMSC-Exo) as an active ingredient for prevention or alleviation of a skin disease.

The cosmetic composition for prevention or alleviation of a skin disease according to the present invention is identical to the pharmaceutical composition for prevention or treatment of a skin disease in terms of active ingredient and target disease, so that a description of overlapping contents therebetween is omitted to avoid excessive complexity of the present specification.

As used herein, the term "alleviation" refers to all acts of improving or beneficially changing symptoms of a disease by administering the composition of the present invention.

The composition of the present invention may be prepared into a cosmetic composition. When the composition comprising an induced pluripotent stem cell-derived mesenchymal stem cells or a culture thereof as an active ingredient for prevention or alleviation of a skin disease according to the present invention is prepared into a cosmetic composition, the cosmetic composition may comprise a commonly used ingredient, for example, an adjuvant and a carrier, such as a stabilizer, a solubilizer, a vitamin, a pigment, and a flavoring, in addition to the induced pluripotent stem cell-derived mesenchymal stem cells or culture thereof as an active ingredient.

The cosmetic composition of the present invention may take any formulation that is usually prepared in the art. Examples of the formulation include a solution, a suspension, an emulsion, a paste, a gel, a cream, a lotion, a powder, a soap, a surfactant-containing cleanser, an oil, a powder foundation, an emulsion foundation, a wax foundation, and a spray, but are not limited thereto. More specifically, the cosmetic composition of the present invention may be prepared in a dosage form of emollient lotion, nourishing lotion, nourishing cream, massage cream, essence, eye cream, cleansing cream, cleansing foam, cleansing water, pack, spray, or powder.

When the formulation of the present invention is a paste, a cream, or a gel, animal oil, vegetable oil, wax, paraffin, starch, tragacanth, cellulose derivatives, polyethylene glycol, silicon, bentonite, silica, talc, or zinc oxide may be used as a carrier ingredient.

For a powder or a spray formulation, the composition of the present invention may comprise lactose, talc, silica, aluminum hydroxide, calcium silicate, or polyamide powder as a carrier ingredient. Particularly when formulated into a spray, the composition of the present invention may further comprise a propellant such as chlorofluorohydrocarbon, propane/butane, or dimethyl ether.

In case of a solution or an emulsion, the composition of the present invention may contain a solvent, a solubilizer, or an emulsifier as a carrier ingredient, as exemplified by water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan.

For a suspension, the composition of the present invention may comprise, as a carrier, a liquid-phase diluent, such as water, ethanol, or propylene glycol; a suspending agent, such as ethoxylated isostearyl alcohol, polyoxyethylene sorbitol ester, or polyoxyethylene sorbitan ester; microcrystalline cellulose; aluminum metahydroxide; bentonite; agar; or tragacanth.

When the composition of the present invention is formulated into a surfactant-containing cleanser, aliphatic alcohol sulfate, aliphatic alcohol ether sulfate, sulfosuccinic acid monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, or ethoxylated glycerol fatty acid ester may be available as a carrier.

An aspect of the present invention provides a method for treating a skin disease in a subject in need thereof, the method comprising administering to the subject a composition comprising induced pluripotent stem cell (iPSC)-derived mesenchymal stem cells (MSC) [iMSC]; a culture thereof; or exosomes derived from iMSC or a culture of iMSC (iMSC-derived exosome, iMSC-Exo) as an active ingredient.

Another aspect of the present invention provides a method for alleviating a skin disease in a subject in need thereof, the method comprising administering to the subject a composition comprising induced pluripotent stem cell (iPSC)-derived mesenchymal stem cells (MSC) [iMSC]; a culture thereof; or exosomes derived from iMSC or a culture of iMSC (iMSC-derived exosome, iMSC-Exo) as an active ingredient. The skin disease, which is a target disease of the treatment method or alleviation method of the present invention, is as defined with respect to the target disease of the pharmaceutical composition.

In an embodiment of the present invention, the subject is a mammal or a human.

The method for treating or alleviating a skin disease according to the present invention uses the same active ingredient as in the above-described composition comprising induced pluripotent stem cell (iPSC)-derived mesenchymal stem cells (MSC) [iMSC]; a culture thereof; or exosomes derived from iMSC or a culture of iMSC (iMSC-derived exosome, iMSC-Exo) as an active ingredient. Thus, a description of overlapping contents therebetween is omitted to avoid excessive complexity of the present specification.

In accordance with still another aspect thereof, the present invention provides exosomes isolated from an induced pluripotent stem cell-derived mesenchymal stem cells or a culture thereof.

The induced pluripotent stem cell-derived mesenchymal stem cells of the present invention have cytological (immunological) traits distinguished from those of conventional mesenchymal stem cells. As described in the Example section of the present invention, comparison was made of expression levels of indoleamine 2,3-dioxygenase (IDO) between general mesenchymal stem cells (MSC) and the induced pluripotent stem cell-derived mesenchymal stem cells (iMSC) of the present invention. As a result, iMSC was observed to express IDO at a higher level than MSC (FIG. 3). In addition, the cultures of MSC and iMSC were separately collected to compare the levels of secretion of inflammation-related cytokine proteins therebetween. iMSC of the present invention showed significantly reduced secretion of IFN-γ, TNF-α, IL-1β, IL-6, and IL-6Rα, compared to MSC (FIG. 4).

In accordance with another aspect thereof, the present invention provides a method for producing exosomes (iMSC-Exo) isolated from induced pluripotent stem cell-derived mesenchymal stem cells (iMSC), the method comprising:

(a) differentiating induced pluripotent stem cells into mesenchymal stem cells;

(b) culturing the mesenchymal stem cells in a cell culture medium; and (c) isolating exosomes from a culture of the mesenchymal stem cells.

A stepwise description will be given of the method for producing induced pluripotent stem cell-derived mesenchymal stem cells.

Step (a): Induction of Differentiation into Mesenchymal Stem Cell

First, induced pluripotent stem cells are induced to differentiate into mesenchymal stem cells.

In an embodiment of the present invention, the differentiation is carried out by culturing induced pluripotent stem cells in an extracellular matrix-coated culture vessel.

As used herein, the term "extracellular matrix" refers to a physical environment for storing and appropriately supplying biochemical factors that cells require for their growth and differentiation and can recognize.

In an embodiment of the present invention, the extracellular matrix is an extracellular matrix protein.

In another embodiment of the present invention, examples of the extracellular protein include vitronectin, fibronectin, laminin, elastin, collagen, and the like, but are not limited thereto.

In a particular embodiment of the present invention, the extracellular protein is vitronectin.

The induction of differentiation from induced pluripotent stem cells to mesenchymal stem cells may be achieved using a cell culture medium containing a differentiation inducing factor (e.g., fetal bovine serum, bFGF, MEM-NEAA, and β-mercaptoethanol).

So long as it is typically available for culturing animal cells, any cell culture medium may be employed. For example, DMEM (Dulbecco's modification of Eagle's medium), a mixture of DMEM and F12, Eagle's MEM (Eagle's minimum essential medium), α-MEM, Iscove's MEM, 199 medium, CMRL 1066, RPMI 1640, F12, F10, Way-mouth's MB752/1, McCoy's 5A, and MCDB series may be available.

Step (b): Culturing of Mesenchymal Stem Cell

Next, the mesenchymal stem cells are cultured in a cell culture medium.

Any of the foregoing mediums available for culturing animal cells may be employed in the cell culturing.

In an embodiment of the present invention, the cell culture medium is a cell culture medium containing exosome-depleted fetal bovine serum. The reason why exosome-depleted fetal bovine serum is contained in the cell culture medium is to prevent the incorporation of exosomes derived from fetal bovine serum contained in the medium other than the exosomes secreted from the mesenchymal stem cells of the present invention because general fetal bovine serum used in cell culturing contains a large amount of exosomes from the exosomes per se.

In another embodiment of the present invention, the culturing is performed for 12-120 hours, 24-96 hours, 48-96 hours, or 60-84 hours, and most particularly for 72 hours, but without limitations thereto.

Step (c): Isolation of Exosome

Finally, exosomes are isolated from a culture of the mesenchymal stem cells.

In an embodiment of the present invention, the exosomes may be isolated from a culture of the mesenchymal stem cells by centrifugation.

More specifically, the culture of mesenchymal stem cells is centrifuged at 200-400×g for 5-20 minutes to remove remaining cells and cell debris. The supernatant is collected and subjected to high-speed centrifugation at 9,000-12,000×g for 60-80 minutes. Then, the resulting supernatant is again collected and subjected to ultracentrifugation at 90,000-120,000×g for 80-100 minutes to obtain exosomes as a pellet. According to a particular embodiment of the present invention, the culture of mesenchymal stem cells is collected, centrifuged at 300×g for 10 minutes to remove remaining cells and cell debris, and then the supernatant is collected, filtered through a 0.22-μm filter, and then centrifuged at 10,000×g and 4° C. for 70 minutes using a high-speed centrifuge. The supernatant thus formed is again collected, and centrifuged at 100,000×g and 4° C. for 90 minutes using an ultracentrifuge to obtain exosomes as a pellet.

In accordance with still another aspect thereof, the present invention provides a stem cell therapy product comprising induced pluripotent stem cell-derived mesenchymal stem cells (iMSCs) or exosomes isolated therefrom (iMSC-exo) as an active ingredient.

As used herein, the term "stem cell therapy product" refers to a pharmaceutical composition comprising stem cells as an active ingredient, and the stem cell therapy product is used for the purpose of tissue regeneration, organ function recovery, or immune cell function control.

In an embodiment of the present invention, the stem cell therapy product is a pharmaceutical composition for prevention or treatment of a disease from which recovery is expected through the pluripotency of the mesenchymal stem cells (e.g., a disease associated with the heart, liver, joint, nervous systems, or immunity).

Since the stem cell therapy product has a component in common with the above-described pharmaceutical composition and cosmetic composition of the present invention, each comprising induced pluripotent stem cell-derived mesenchymal stem cells, a culture thereof, or exosomes isolated therefrom, a description of overlapping contents therebetween is omitted to avoid excessive complexity of the present specification.

Advantageous Effects

Features and advantages of the present invention are summarized as follows.

(a) The present invention provides a pharmaceutical composition for prevention or treatment of a skin disease and a cosmetic composition for prevention or alleviation of a skin disease, each composition comprising induced pluripotent stem cell-derived mesenchymal stem cells, a culture thereof, or exosomes isolated therefrom as an active ingredient.

(b) The present invention provides induced pluripotent stem cell-derived mesenchymal stem cells, a culture thereof, or exosomes isolated therefrom and a stem cell therapy product comprising induced pluripotent stem cell-derived mesenchymal stem cells (iMSCs) or exosomes isolated therefrom as an active ingredient.

(c) The use of the compositions of the present invention can provide compositions and a stem cell therapy product for a skin disease, each having an improved immunomodulatory function, compared with those using existing mesenchymal stem cells.

DETAILED DESCRIPTION

Hereinafter, the present invention will be described in more detail with reference to examples. These examples are only for illustrating the present invention more specifically, and it would be apparent to those skilled in the art that the scope of the present invention is not limited by these examples according to the gist of the present invention.

Unless otherwise stated, the "%" used to express the concentration of a specific material refers to (wt/wt) % for solid/solid, (wt/vol) % for solid/liquid, and (vol/vol) % for liquid/liquid throughout the present specification.

Example 1

Figure 1:
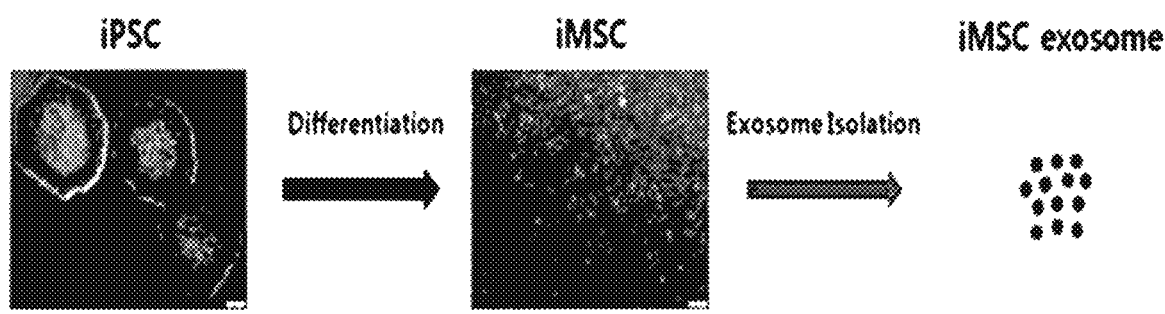
FIG. 1 schematically shows the preparation of induced pluripotent stem cell-derived mesenchymal stem cells (iMSC) and exosomes derived from the mesenchymal stem cells (iMSC-exo).

Preparation and Assay of Induced Pluripotent Stem Cell-Derived Mesenchymal Stem Cell Induced pluripotent stem cells (induced pluripotent stem cells (iPSC) originated from fibroblasts, peripheral blood mononuclear cells (PBMC), and mesenchymal stem cells (MSC), established by Asan Medical Center (AMC, Stem Cell Center, Seoul), which were cultured in DMEM/F-12 supplemented with Knockout xeno-free serum replacement, glutamax, non-essential amino acids, beta-mercaptoethanol, antibiotic, and basic fibroblast growth factor (bFGF) without the use of feeder cells, were allowed to adhere to culture dishes previously coated with vitronectin and then induced to differentiate into mesenchymal stem cells in a DMEM medium supplemented with 10% FBS (v/v), 5 ng/ml basic FGF, 0.1 mM MEM NEAA (Minimum Essential Media Non-Essential Amino Acids), β-mercaptoethanol (1×), 100 units/ml penicillin, and 100 μg/ml streptomycin at 37° C. On day 7 of culturing, the cells were dissociated into single cells by treatment with TrypLE express (1×), transferred onto cell culture plates, and then further incubated for 7 days. While the medium was freshly exchanged every two days, an observation was made of the differentiation into mesenchymal stem cells (iMSC) with a flat and elongated appearance (FIG. 1).

Figure 2:
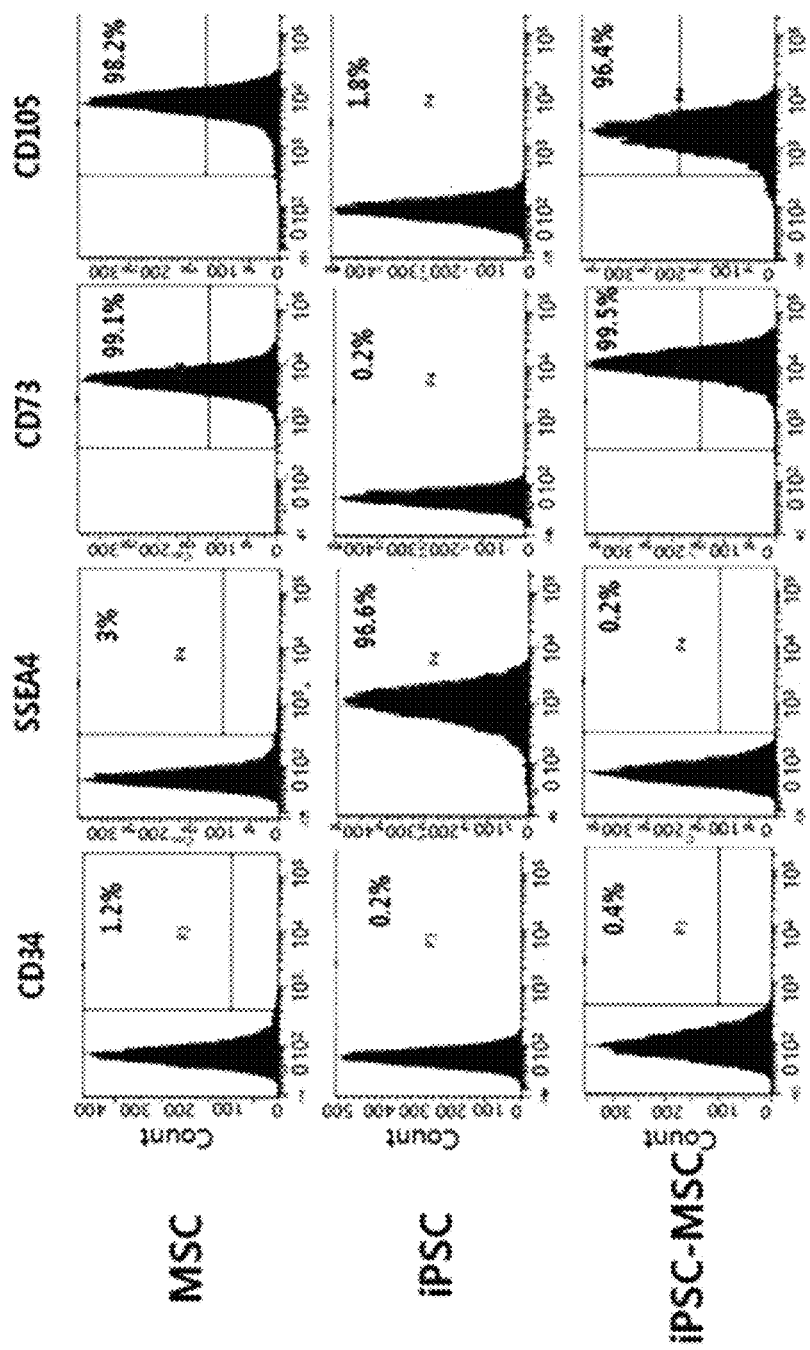
FIG. 2 shows analysis results of surface antigens on MSC, iPSC, and iMSC.

After completion of the induction of differentiation into mesenchymal stem cells (iMSC) for 14 days, the cells were assayed for the negative expression of the mesenchymal stem cell-specific surface antigen markers CD34 (BD Biosciences, Catalog No.: 348053) and SSEA4(BD Biosciences, Catalog No.: 560128) and the positive expression of the mesenchymal stem cell-specific surface antigen markers CD73 (BD Biosciences, Catalog No.: 550257) and CD105 (BD Biosciences, Catalog No.: 560839), using flow cytometry. As a result, the iMSC was found to have typical characteristics of mesenchymal stem cells (MSC), that is, negative for CD34 and SSEA4 and positive for CD73 and CD105 (FIG. 2). The mesenchymal stem cells isolated from fetal umbilical tissues and established by AMC Stem Cell Center were used as a control.

Figure 3:
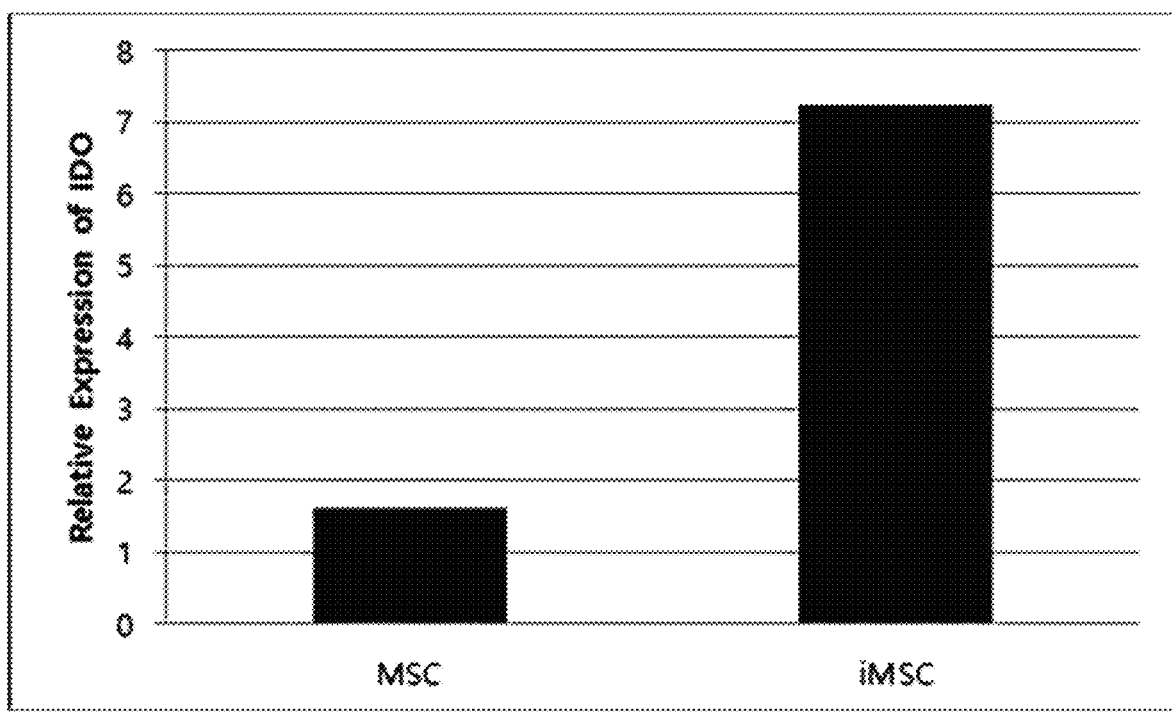
FIG. 3 shows expression levels of IDO in MSC and iMSC.

In addition, indoleamine 2,3-dioxygenase (IDO) in MSC and iMSC was quantitated using real-time PCR. A higher expression level of IDO was detected in iMSC than MSC (FIG. 3).

TABLE 1

Sequences of primers for detection of indoleamine 2,3-dioxygenase (IDO)

| | |
|---|---|
| Forward primer (SEQ ID NO: 1) | 5'-GCCCTTCAAGTGTTTCACCAA-3' |
| Reverse primer (SEQ ID NO: 2) | 5'-GCCTTTCCAGCCAGACAAATAT-3' |

Indoleamine 2,3-dioxygenase, which is an enzyme converting tryptophan into kynurenine, is known to suppress inflammation and immune responses by depleting tryptophan in the periphery of cells and inhibiting the proliferation of immune cells. It is thus understood that the iMSC of the present invention with high IDO expression has high inhibitory activity against immune responses.

In addition, the cultures of MSC and iMSCs were separately collected to measure and compare levels of secretion of inflammation-related cytokine proteins therebetween.

Inflammation-related cytokines were measured according to Magnetic Luminex® Screening Assay. First, cultures of MSCs and iMSCs were vortexed and then centrifuged, and the supernatants were ½ diluted with a diluent. Each of the samples thus prepared was incubated with the bead-Ab mixture at room temperature for 2 hours. After completion of the reaction, the cytokines were measured by the Luminex instrument (Luminex, Austin, Tex., USA).

The analytes in the sample reacted with corresponding antibodies attached to particularly numbered beads, respectively and independently while the detection antibody reacted with 2'(streptavidin-PE) (sandwich assay). For the assay results, the fluorescence level of phycoerythrin (PE) attached to the corresponding bead surface in proportion to the amount of each analyte was measured. While flowing the beads one by one, the Luminex instrument checked the bead number and measured the PE fluorescence intensity of the bead surface to obtain a reaction result value (MFI) of each analyte. A standard curve was made by the best fit method in the calculation software "MasterPlex QT 2010 (MiraiBio, Hitachi, Calif., USA)" from the reaction measurement value (MFI) for each standard concentration, and on the basis of the standard curve, the resultant concentration value of the corresponding sample was calculated by reflecting the dilution factor.

Figure 4:
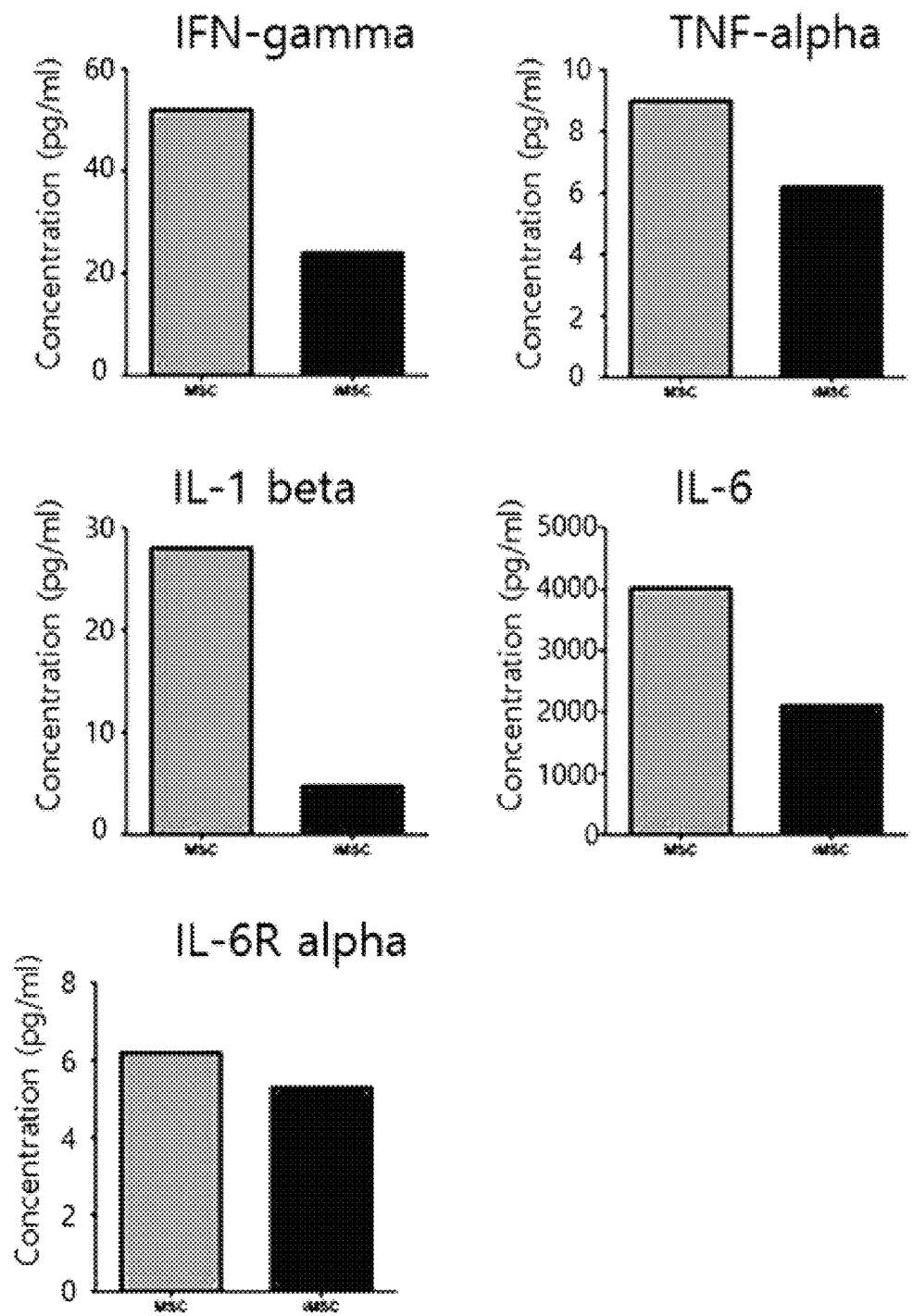
FIG. 4 shows levels of cytokine secretion from MSC and iMSC.

As a result, iMSC secreted IFN-γ, TNF-α, IL-1β, IL-6, and IL-6Rα at low levels, compared to MSC (FIG. 4).

From the results, it is understood that the induced pluripotent stem cell-derived mesenchymal stem cells (iMSC) of the present invention are novel mesenchymal stem cells having cytological (immunological) traits distinguished from those of existing MSC.

Example 2

Isolation and Verification of Exosomes from Induced Pluripotent Stem Cell-Differentiated Mesenchymal Stem Cells iMSC identified to have traits of mesenchymal stem cells was additionally cultured in a culture medium supplemented with 10% exosome-depleted FBS. After incubation for 72 hours, the culture of iMSC was collected and centrifuged at 300×g for 10 minutes to remove cells and cell debris. The supernatant was filtered using a 0.22-μm filter, and then centrifuged at 10000×g for 70 minutes at 4° C. in a high-speed centrifuge. The supernatant thus obtained was centrifuged at 100,000×g and 4° C. for 90 minutes in an ultracentrifuge to obtain exosomes as a pellet. The exosomes were diluted in phosphate buffered saline (PBS) before use.

Figure 5:
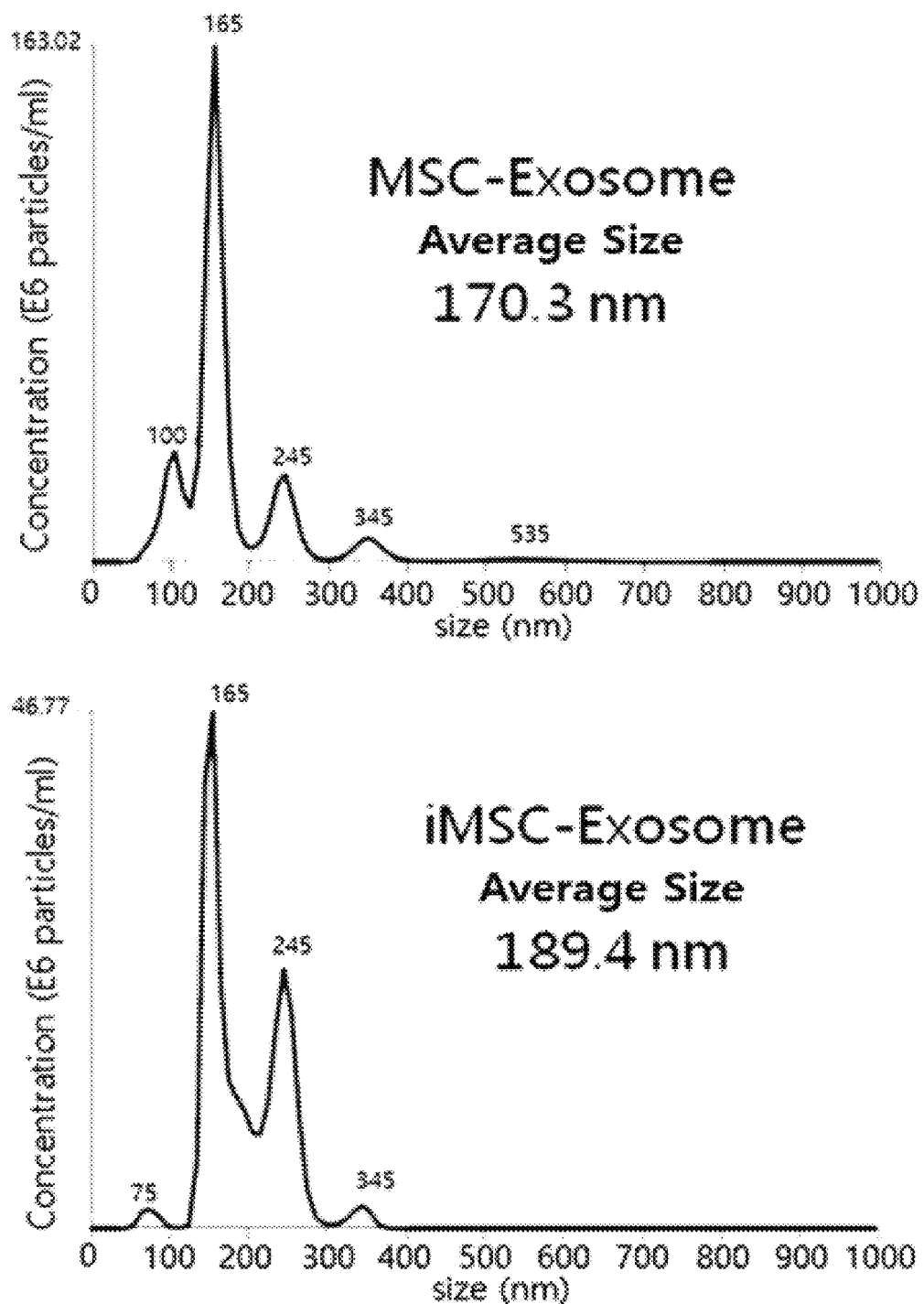
FIG. 5 shows sizes of exosomes isolated from mesenchymal stem cells (MSC-Exo) and from induced pluripotent stem cell-derived mesenchymal stem cells (iMSC-exo).
Figure 6:
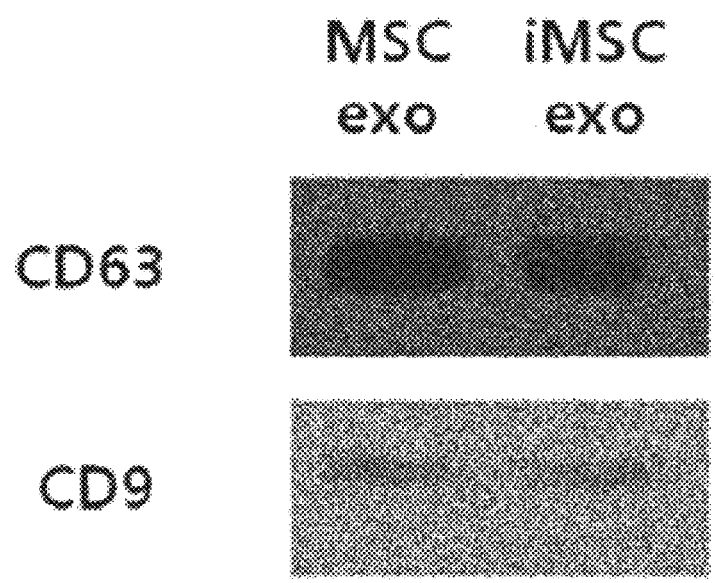
FIG. 6 shows the expression of CD63 and CD9 in MSC-Exo and iMSC-exo.
Figure 7:
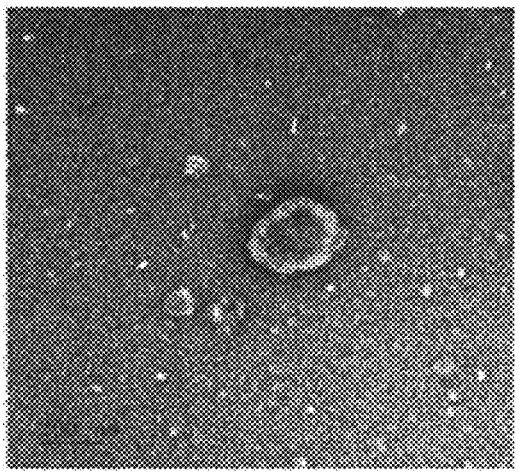
FIG. 7 shows electron microscope images of MSC-Exo and iMSC-Exo.
Figure 7:
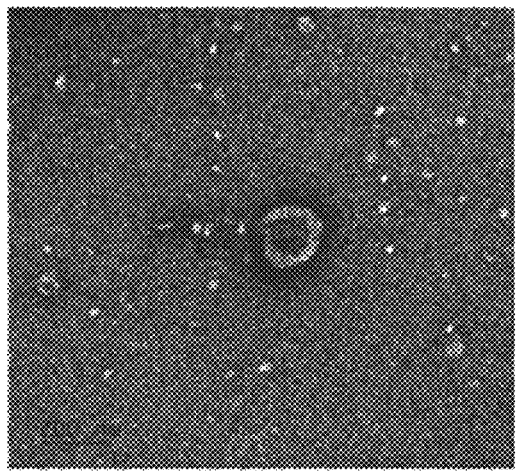

The exosomes respectively isolated from the cultures of MSC and iMSC were counted and analyzed for size distribution by using nanoparticle tracking assay (NanoSight NS300, Malvern) (FIG. 5). The expression of CD9 and CD63, which are exosome-specific surface antigens, was verified by western blotting (FIG. 6) and morphological observation was made of the exosomes under an electron microscope (FIG. 7).

It could be therefore confirmed that the exosomes respectively derived from MSC and the iMSC of the present invention had the traits of exosomes themselves.

Example 3

Construction of Atopic Disease-Induced Mice and Administration Thereto

As experimental animals, 8-week-old BALB/c female mice were purchased (Orient Bio, South Korea) and acclimated for 1 week before use. For the induction of atopic dermatitis, the backs of the BALB/c mice at 9 weeks of age were shaved to the upper part as much as possible by a shaver. An *Aspergillus fumigates* (Af) extract (40 μg) was applied to the shaved dorsal skin tissue (1×1 cm$^2$) at intervals of 24 hours for 5 days. After a 2-week rest period, the extract was repeatedly applied five times at intervals of 24 hours from day 19, to thereby establish atopic dermatitis animal models.

Figure 8:
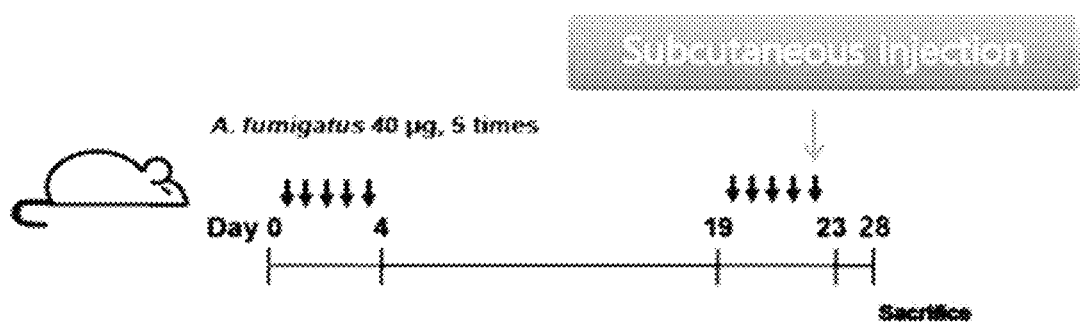
FIG. 8 is a scheme for constructing an atopic dermatitis animal model.

After establishment of atopic dermatitis animal models, MSC, iMSC, MSC-Exo (exosomes from mesenchymal stem cells) or iMSC-Exo (exosomes from induced pluripotent stem cell-derived mesenchymal stem cell) was subcutaneously injected. MSC or iMSC was injected at a dose of 2×10$^6$ cells per animal, and MSC-exo or iMSC-exo was injected at a dose of 12 μg per animal. The mice were sacrificed and analyzed on day 5 after the injection (FIG. 8).

Example 4

Figure 9:
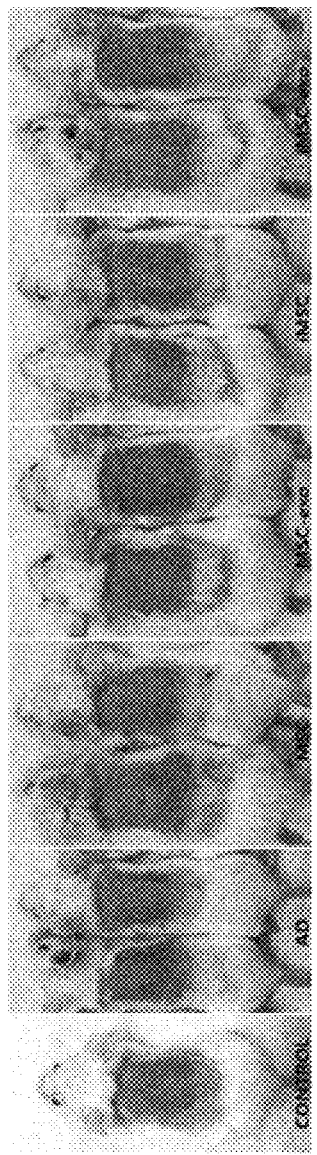
FIG. 9 shows effects of iMSC and iMSC-exo on atopic lesions of atopic dermatitis animal models.

Evaluation of Therapeutic Effect of Induced Pluripotent Stem Cell-Derived Mesenchymal Stem Cell (iMSC) and Exosome from Induced Pluripotent Stem Cell-Derived Mesenchymal Stem Cell (iMSC-Exo) on Atopic Dermatitis (1) Atopic Symptom Alleviation To investigate the atopy alleviation levels of iMSC and iMSC-exo, a negative control group without atopic dermatitis (CONTROL, physiological saline treated), a positive control group with atopic dermatitis (AD, Af-treated), an MSC-treated group, an MSC-Exo-treated group, an iMSC-treated group, and an iMSC-Exo-treated group were observed and compared. As a result, the iMSC-treated group and the iMSC-Exo-treated group showed an atopy alleviation effect at similar levels, compared with the negative control group (FIG. 9).

The data demonstrate that iMSC and iMSC-Exo of the present invention have excellent alleviative or therapeutic effects on skin disease including atopic dermatitis.

(2) Skin Clinical Scores and Transepidermal Water Loss Evaluation

Figure 10:
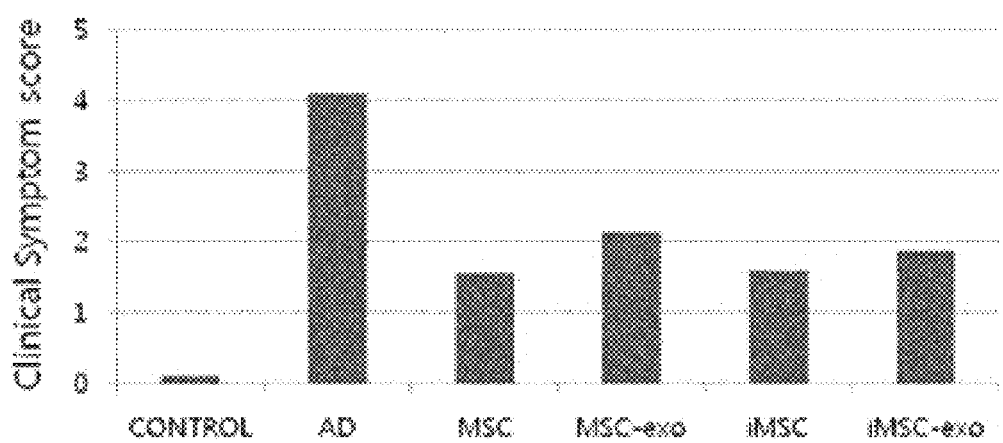
FIG. 10 shows skin clinical scores resulting from iMSC and iMSC-exo treatment in atopic dermatitis animal models.

Skin clinical scores were set according to five items: dryness, scaling, erosion, excoriation, and hemorrhage. In each item, scores were assigned: 0 point for lesion-free condition; 1 point for a mild condition, 2 points for a moderate condition; and 3 points for a severe condition. The corresponding points were summed up to calculate a skin clinical score. As a result, the iMSC-treated group and the iMSC-exo-treated group showed lower skin clinical scores compared with the positive control group (AD), the MSC-treated group, or the iMSC-exo-treated group (Table 2 and FIG. 10).

TABLE 2

Skin clinical scores

| CONTROL | AD | MSC | MSC-exo | iMSC | iMSC-exo |
|---|---|---|---|---|---|
| 0.1 | 4.1 | 1.6 | 2.1 | 1.6 | 1.8 |

Figure 11:
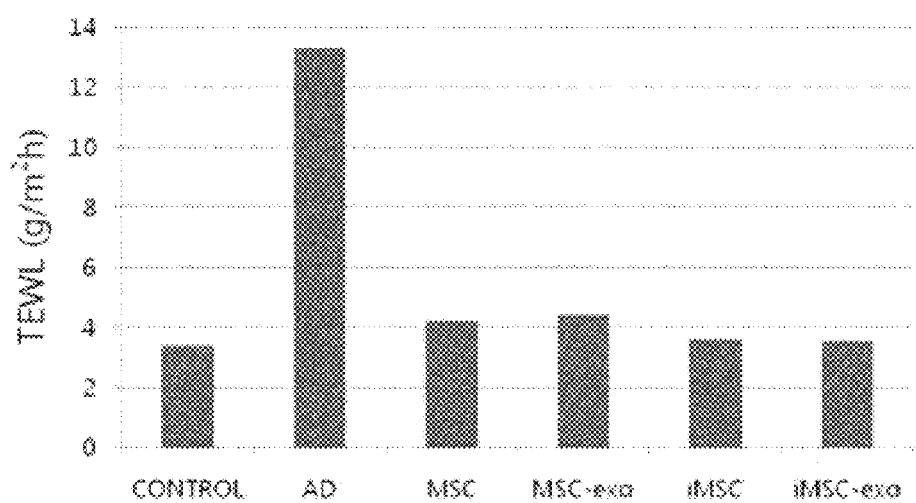
FIG. 11 shows the transepidermal water loss resulting from iMSC and iMSC-exo treatment in atopic dermatitis animal models.

To evaluate skin barrier damage in the same administration groups, the transepidermal water loss (TEWL) was measured using VapometerSWL-3® (Delfin technologies). As understood from the data, the iMSC-treated group and the iMSC-Exo-treated group showed remarkably reduced levels of transepidermal water loss (TEWL), compared with the positive control (AD) the negative control (CONTROL), the MSC-treated group, and the MSC-Exo-treated group, indicating the improvement in atopic symptoms (Table 3 and FIG. 11).

TABLE 3

Transepidermal water loss (TEWL) levels

| CONTROL | AD | MSC | MSC-Exo | iMSC | iMSC-Exo |
|---|---|---|---|---|---|
| 3.4 | 13.3 | 4.2 | 4.4 | 3.6 | 3.5 |

Therefore, the iMSCs and iMSC-Exo of the present invention alleviate skin clinical symptoms and significantly reduce transepidermal water loss levels, thereby showing excellent effects of alleviating or treating of skin diseases including atopic dermatitis.

(3) Skin Histological Observation

Figure 12:
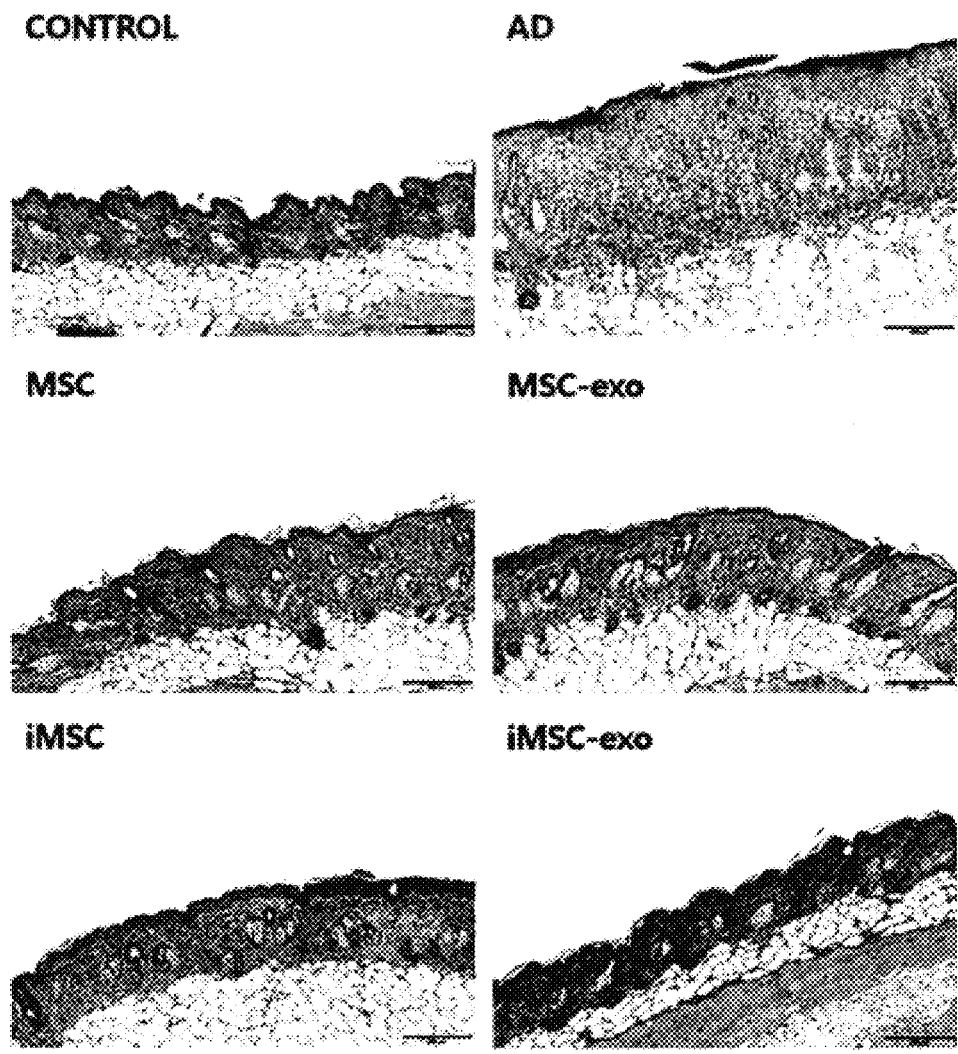
FIG. 12 shows skin histological changes by iMSC and iMSC-exo treatment in atopic dermatitis animal models. The scale bars mean 200 μm.

Skin tissues were isolated from the negative control group, the positive control group, the MSC-treated group, the MSC-Exo-treated group, the iMSC-treated group, and the iMSC-Exo-treated group. The isolated skin tissues were fixed with 10% formalin solution, embedded in paraffin, and then cut into sections 5 μm thick. To investigate skin histological changes and inflammatory cell invasion, the skin sections were stained with hematoxylin and eosin and observed under a microscope at 400× magnification. As a result, stratum corneum damage and the thickness of epidermal and dermal layers were reduced in the iMSC-treated group and the iMSC-Exo-treated group, compared with the positive control group (FIG. 12).

The data demonstrate that the iMSC and iMSC-Exo of the present invention alleviate stratum corneum damage and reduce the thickness of epidermal and dermal layers, thereby showing excellent effects of alleviating or treating skin diseases including atopic dermatitis.

(4) Serum IgE Measurement

Figure 13:
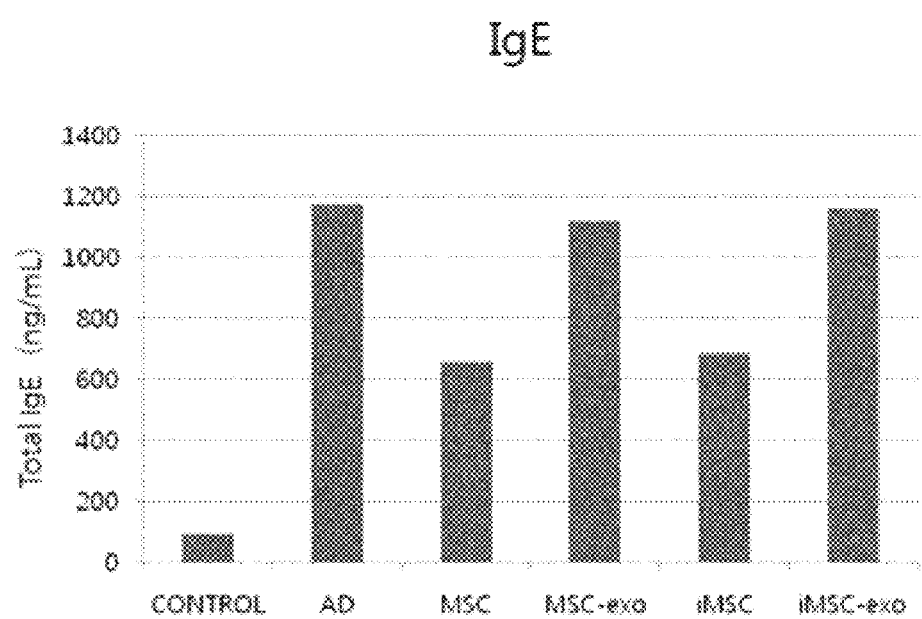
FIG. 13 shows serum IgE levels by iMSC and iMSC-exo treatment in atopic dermatitis animal models.

Mice in the negative control group, the positive control group, the MSC-treated group, the MSC-Exo-treated group, the iMSC-treated group, and the iMSC-Exo-treated group were each cut to open the abdomen, and about 0.5-0.7 mL of blood was collected from the postcaval vein after needle insertion. Sera was separated from the isolated blood by centrifugation. The total IgE level in each separated serum was measured using an ELISA test kit (eBioscience). The serum IgE level was reduced in the iMSC-treated group, compared with the positive control group, but with no significant changes in the iMSC-Exo-treated group (FIG. 13).

It is understood from the above results and clinical symptom improvement effects in the above-described Examples that the skin disease alleviating efficacy of the iMSC, and iMSC-Exo of the present invention is not mainly medicated by IgE.

(5) Verification of T Cell Immune Response

Figure 14:
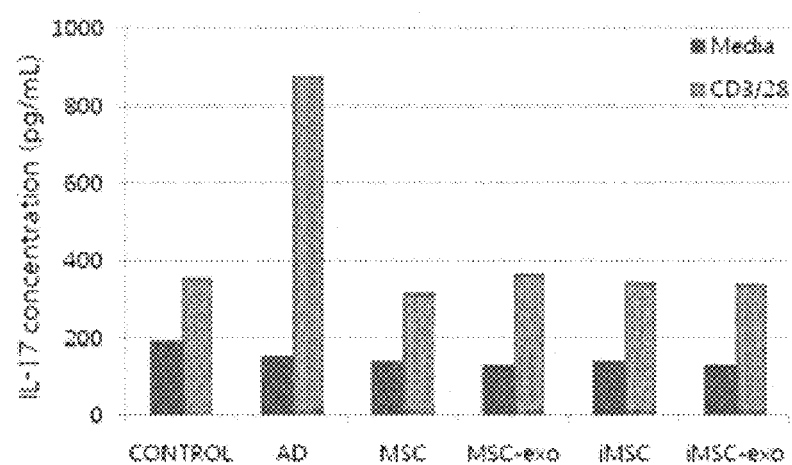
FIG. 14 shows levels of IL-17a secretion from lymphocytes by iMSC and iMSC-exo treatment in atopic dermatitis animal models.

To investigate T cell immune responses of iMSC and iMSC-Exo, lymphocytes were isolated from lymph nodes of the mice in the negative control group, the positive control group, the iMSC-treated group, and the iMSC-exo-treated group. After the isolated lymphocytes were stimulated by CD3/CD28, the cultures thereof were collected. Cytokine secretion was measured using an ELISA kit (eBioscience). As for IL-17A, a main cytokine produced in Th17, its expression levels in the iMSC-treated group and the iMSC-Exo-treated group were similar to that in the negative control, but significantly lowered compared to the positive control (FIG. 14).

It is inferred on the basis of the above results and the clinical symptom improvement effects and serum IgE level changes in the above-described Examples that the skin disease alleviation efficacy of the iMSC and iMSC-Exo of the present invention was not mainly mediated by IgE, but by inhibiting immune responses of T cells, such as IL-17A.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method for treating or alleviating a skin disease in a subject in need thereof, comprising:
    administering to the subject a composition comprising an effective amount of one or more exosomes isolated from induced pluripotent stem cell-derived mesenchymal stem cells or a culture thereof,
    wherein the skin disease is selected from the group consisting of atopic dermatitis and contact dermatitis.

2. The method of claim 1, wherein the subject is a mammal or a human.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Forward primer for detection of human indoleamine 2,3-dioxygenase gene

```
<400> SEQUENCE: 1
gcccttcaag tgtttcacca a                                        21

<210> SEQ ID NO 2
<211> LENGTH: 22
<212> TYPE: DNA
<213> ORGANISM: Artificial Sequence
<220> FEATURE:
<223> OTHER INFORMATION: Reverse primer for detection of human
      indoleamine 2,3-dioxygenase gene

<400> SEQUENCE: 2
gcctttccag ccagacaaat at                                       22
```